United States Patent

Gschwend et al.

[11] 4,187,313
[45] Feb. 5, 1980

[54] 2-AMINOETHYL-1,4-BENZODIOXANS

[75] Inventors: Heinz W. Gschwend, New Providence; Charles F. Huebner, Chatam, both of N.J.

[73] Assignee: Ciba-Geigy Corporation, Ardsley, N.Y.

[21] Appl. No.: 949,583

[22] Filed: Oct. 10, 1978

Related U.S. Application Data

[63] Continuation-in-part of Ser. No. 873,457, Jan. 30, 1978, abandoned.

[51] Int. Cl.² .................. A61K 31/335; C07D 319/08
[52] U.S. Cl. .................. 424/278; 260/340.3; 260/348.25; 260/570.8 R; 260/600 R; 560/60
[58] Field of Search ...................... 260/340.3; 424/278

[56] References Cited

U.S. PATENT DOCUMENTS

| | | | |
|---|---|---|---|
| 2,551,013 | 5/1951 | Kerwin | 260/340.3 |
| 3,312,592 | 4/1967 | Chodnekar et al. | 424/278 |
| 3,324,143 | 6/1967 | Mold et al. | 260/340.3 |
| 3,444,210 | 5/1969 | Mold et al. | 260/340.3 |

OTHER PUBLICATIONS

Howe et al., Journ. Med. Chem., 13(2), pp. 169–176 (1970).
Chem. Abstracts 79:126411j.

*Primary Examiner*—Ethel G. Love
*Attorney, Agent, or Firm*—Theodore O. Groeger

[57] ABSTRACT

Specific optical isomers of 2-(2-aralkylamino-1-hydroxyethyl)-1,4-benzodioxans, e.g., those of the formula

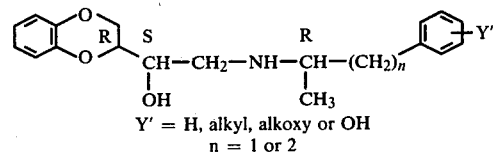

Y' = H, alkyl, alkoxy or OH
n = 1 or 2 and salts thereof are antihypertensive and bradycardic agents.

7 Claims, No Drawings

2-AMINOETHYL-1,4-BENZODIOXANS

CROSS-REFERENCE TO RELATED APPLICATION

This is a continuation-in-part of application Ser. No. 873,457, filed Jan. 30, 1978 (now abandoned).

BACKGROUND OF THE INVENTION

Complex mixtures of said isomers are disclosed in U.S. Pat. No. 3,312,592; J. Med. Chem. 13, 169 (1970) or Chem. Abstr. 79, 126411j (1973) as β-adrenergic blocking, sympatholytic and adrenolytic agents for the treatment of prophylaxis of coronary artery diseases. Said mixtures of at least eitht erythro- and threo-diastereomeric forms cannot be separated easily. Due to our new process for suitably substituted erythro forms of 2-(1-hydroxyethyl)-1,4-benzodioxan intermediates it is possible to obtain simple mixtures of said isomers, which can be separated more readily.

Surprisingly, it was found that only the above-specified R, S, R-diastereomers exhibit said valuable pharmacological effects, whereas the S, R, S—; S, R, R— and R, S, S— analogs are merely contributing to their side effects, e.g. toxicity.

SUMMARY OF THE DISCLOSURE

The present invention concerns and has for its object the provision of specific diastereomers of erythro-2-(2-aralkylamino-1-hydroxyethyl)-1,4-benzodioxans corresponding to Formula I $$X_p\text{-benzodioxan-}R\overset{S}{\underset{\underset{OH}{|}}{CH}}-CH_2-NH-\overset{R}{\underset{\underset{C_mH_{2m+1}}{|}}{CH}}-(CH_2)_n\text{-phenyl-}Y_q \quad (I)$$

wherein each of X and Y are hydrogen, hydroxy, lower alkyl, lower alkoxy, lower alkylthio, halogen or trifluoromethyl; each of p and q is the integer 1 or 2 and each of m and n is an integer from 1 to 4; of pharmaceutically acceptable acid addition salts thereof; as well as of corresponding pharmaceutical compositions and of methods for the preparation and application of these products, which are useful antihypertensive and bradycardic agents.

DESCRIPTION OF THE PREFERRED EMBODIMENTS

The term "lower," referred to above and hereinafter in connection with organic radicals or compounds respectively, defines such with up to 7, preferably up to 4 carbon atoms.

Accordingly, a lower alkyl group X and/or Y is preferably methyl, but also, for example, ethyl, n- or i-propyl or butyl; lower alkoxy represents especially methoxy but also ethoxy, n- or i-propoxy or butoxy; lower alkylthio is illustrated by melthyl or ethylthio; and halogeno by fluoro, chloro or bromo.

The integers m, p and q are preferably but one, and n especially one or two.

Pharmaceutically acceptable acid addition salts of the bases of Formula I are preferably derived from strong inorganic or organic acids, e.g., those listed below.

The compounds of the invention exhibit valuable pharmacological properties, primarily hypotensive, antihypertensive and bradycardic effects, inter alia due to their α- and β-adrenergic blocking, vasodilating and inhibitory activity of central sympathetic outflow. This is demonstrable in animal tests, using advantageously mammals, e.g., rats, cats or dogs, as test objects. The animals may either be normotensive or hypertensive, e.g., genetically hypertensive rats. Said compounds can be applied to them enterally or parenterally, advantageously orally or intraveneously, for example within gelatin capsules or in the form of starchy suspensions or aqueous solutions respectively. The applied dosage may range between about 0.01 and 50 mg/kg/day, preferably between about 0.1 and 10 mg/kg/day, advantageously between about 1 and 5 mg/kg/day. The lowering effect on the blood pressure is recorded either directly by means of a catheter, for example placed in the dog's femoral artery, or indirectly by sphygmomanometry at the rat's tail, and a transducer, expressing the blood pressure prior and after dosing in mm Hg. Thus, for example, the 1-erythro-2R-[2-(4-phenyl-2R-butylamino)-1S-hydroxyethyl]-1,4-benzodioxan, a representative member of the compounds of the invention, advantageously in the form of the hydrochloride thereof, is very effective in said hypertensive rats at p.o.-doses as low or lower than 5 mg/kg/day and bradycardic effects on electrically stimulation-induced elevations in the heart rate of anesthetised, bilaterally vagotomized mongrel dogs can be recorded after a single i.v.-dose as low as 0.03 mg/kg. Accordingly, the compounds of the invention are useful antihypertensive and bradycardic agents, for example in the treatment or management of primary or secondary hypertension, angina pectoris or chronic hypertension. They are also useful intermediates in the preparation of other valuable products, especially of pharmacologically active compositions.

Particularly useful for said purpose are compounds of Formula I, wherein each of X and Y are hydrogen, hydroxy, fluoro, chloro, trifluoromethyl or alkyl, alkoxy or alkylthio each with up to 4 carbon atoms, p is the integer 1, q is 1 or 2 and each of m and n is the integer 1 or 2; or pharmaceutically acceptable acid addition salts thereof.

More preferred are the compounds of Formula II $$\text{benzodioxan-}R\overset{S}{\underset{\underset{OH}{|}}{CH}}-CH_2-NH-\overset{R}{\underset{\underset{CH_3}{|}}{CH}}-(CH_2)_n\text{-phenyl-}Y' \quad (II)$$

wherein Y' is hydrogen, hydroxy, alkyl or alkoxy with up to 4 carbon atoms and n is the integer 1 or 2; or pharmaceutically acceptable acid addition salts thereof.

The compounds of the invention are prepared according to methods known per se, advantageously by:

(1) condensing compounds of Formulae III and IV $$X_p\text{-benzodioxan-}R\overset{S}{\underset{\underset{Z_1}{|}}{CH}}-CH_2-Z_2+Z_3-\overset{Q}{\underset{\underset{C_mH_{2m+1}}{|}}{CH}}-(CH_2)_n\text{-phenyl-}Y_2$$

(III)                      (IV)

wherein $Z_1$ is hydroxy and one of $Z_2$ and $Z_3$ is reactively esterified hydroxy and the other is free or metallized primary amino, or $Z_1$ and $Z_2$ together represent epoxy and $Z_3$ is primary amino, Q represents the absolute configuration R when $Z_3$ is said amino group, or Q stands for the S-configuration when $Z_3$ has said other meaning, due to Walden-inversion.

Said reactively esterified hydroxy group $Z_2$ or $Z_3$ is preferebly derived from a strong inorganic or organic acid, such as a hydrohalic, e.g. hydrochloric, hydrobromic or hydriodic acid; or an aliphatic or aromatic sulfonic acid, e.g. methane, p-toluene or m-bromobenzene sulfonic acid. The metalllized amino group $Z_3$ or $Z_2$ is preferably derived from alkali metals, e.g., sodium or potassium.

Said condensation with reactive esters is advantageously carried out in the presence of basic condensing agents, such as alkali or alkaline earth metal hydroxides or carbonates, lower alkali metal alkoxides or tertiary nitrogen bases, such as lower dialkylamines, pyridine, quinoline or their lower alkylated derivatives. The condensation of said epoxides III does not require condensing agents, but merely elevated temperatures, e.g., up to about 100°–150°, whereas said reactive esters may be condensed with the amines between about 0° and 150°.

The starting material of Formula III is preferably prepared according to our new process which comprises the following steps:

(a)

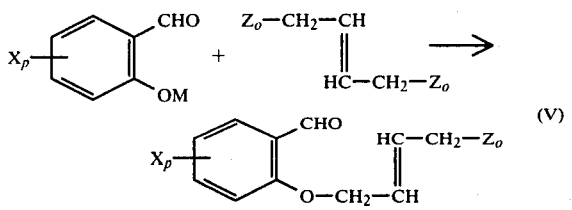

wherein M is one equivalent of a metal atom and $Z_0$ a halogen atom;

(b)

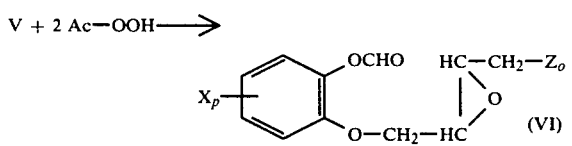

wherein Ac is lower alkanoyl, haloalkanoyl, unsubstituted or substituted benzoyl or phthaloyl, e.g., such containing one or two of said substituent X;

(c)

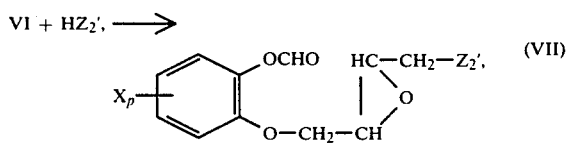

wherein $Z_2'$, is said reactively esterified hydroxy or primary amino group excluding $Z_0$;

(d)

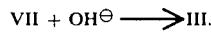

In the above reactions M represents preferably an alkali metal, e.g., lithium, sodium or potassium and the hydroxy ion in step (d) is preferably provided from such metal hydroxide, e.g., potassium hydroxide, or of a strong quaternary nitrogen base, such as lower trialkylbenzylammonium hydroxide. $Z_0$ represents above all chloro, but also bromo or iodo. The percarboxylic acid AcOOH is, for example, peracetic, trifluoroperacetic, perbenzoic, m-chloroperbenzoic or mono-perphthalic acid. The peroxidation should be carried out in low boiling haloalkanes, e.g., methylene chloride for said aromatic peracids, or lower alkyl alkanoates for the aliphatic peracids.

Said starting material of Formula III, wherein $Z_1$ and $Z_2$ together represent epoxy, may also be prepared according to our new process comprising the condensation of compounds of the formulae

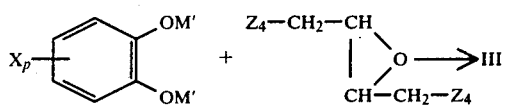

wherein M' is one equivalent of a strong base, preferably an alkali metal atom, or the ion of a strong tertiary or quaternary nitrogen base and $Z_4$ is reactively esterified hydroxy, e.g. that mentioned for $Z_2$ or $Z_3$, advantageously in the presence of diluents, such as lower alkylformamides or -sulfoxides and between about 50° and about 70°.

The d,l-erythro-compounds III so obtained, comprising the R,S— and S,R— enantiomers, can be separated with the use of optically active acids, such as mandelic or tartaric acid or camphor sulfonic acid and the like, which are either salt-forming with the amino group $Z_2$, or esterifying said hydroxy group therein. Such separation is advantageously carried out as described under item (3) below.

The compounds of the invention can also be prepared by:

(2) chiral reduction of compounds of the Formula VIII

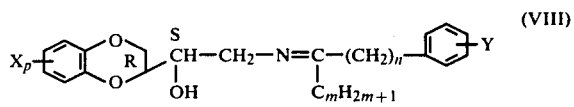

with complex, chiral alkali metal organoboranes oralanes, such as lithium β-isopinocampheyl-9-borabicyclo[3,3,1]nonylhydride or substitution products of lithium aluminumhydride with chiral bases, e.g. ephedrin or amphetamines, and reducing as usual.

The Schiff's bases VIII are obtained from the amines III and corresponding ketones which are either known, or obtainable from the known alcohols IV with $Z_3$=OH, by methods known per se, e.g., oxidation with chromic acid or its anhydride.

Finally, the compounds of the invention can be prepared by:

(3) recrystallization of the erythro-mixture of diastereomeric salts corresponding to Formula I and comprising the R,S,R— and S,R,R,-diastereomers, derived from the pharmaceutically acceptable acids mentioned below. The hydrochloride of the desired R—S—R-stereoisomer comes out of solution preferentially, leaving the undesired S—R—R-stereoisomer in solution.

Said recrystallization is preferably carried out in anhydrous or aqueous lower alkanols, such as ethanol, i- or n-propanol.

The starting material is prepared similar to processes (1) or (2) but using instead of optically pure R,S- compounds of Formulae III or VIII, the corresponding (erythro) R,S- or S,R-mixtures thereof, obtainable according to the process-steps (a) to (d), optionally followed by the Schiff's base formation (VIII).

The compounds of the invention are either obtained in the free, basic form, or as a salt thereof. Any resulting base can be converted into a corresponding acid addition salt, preferably with the use of a pharmaceutically useful acid or anion exchange preparation, or resulting salts can be converted into the corresponding free bases, for example, with the use of a stronger base, such as a metal or ammonium hydroxide, basic salt or cation exchange, e.g. an alkali metal hydroxide or carbonate. Said acid addition salts are preferably such of pharmaceutically acceptable inorganic or organic acids, such as strong metalloidic acids, for example hydrohalic, e.g., hydrochloric of hydrobromic acid; sulfuric, phosphoric, nitric or perchloric acid; aliphatic or aromatic carboxylic or sulfonic acids, e.g., formic, acetic, propionic, succinic, glycollic, lactic, malic, tartaric, citric, ascorbic, maleic, hydroxymaleic, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, ethylenesulfonic, halogen-benzenesulfonic, toluenesulfonic, naphthalenesulfonic, sulfanilic or cyclohexylsulfamic acid. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure.

The invention further includes any variant of the present process, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially valuable, e.g., those of Formula II.

The pharmacologically active compounds of the invention are useful in the manufacture of pharmaceutical compositions comprising an effective amount thereof in conjunction or admixture with excipients suitable for either enteral or parenteral administration. Preferred are tablets and gelatin capsules comprising the active ingredient together with (a) diluents, e.g., lactose, dextrose, sucrose, mannitol, sorbitol, cellulose and/or glycine, (b) lubricants, e.g., silica, talcum, stearic acid, its magnesium or calcium salt and/or polyethyleneglycol, for tablets also (c) binders, e.g., magnesium aluminum silicate, starch paste, gelatin, tragacanth, methylcellulose, sodium carboxymethylcellulose and/or polyvinylpyrrolidone, if desired, (d) disintegrants, e.g., starches, agar, alginic acid or its sodium salt, enzymes of the binders or effervescent mixtures and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods respectively, and contain about 0.1 to 90%, preferably about 1 to 75%, of the active ingredient. A unit dosage for a mammal of about 50 to 70 kg weight may contain between about 10 and 100 mg of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mmHg.

EXAMPLE 1

The mixture of 11.0 g of d,l-erythro-2-oxiranyl-1,4-benzodioxan and 9.2 g of l-3R-amino-1-phenylbutane is heated to 100° for 4 hours while stirring under nitrogen. It is dissolved in 100 ml of 2-propanol while still warm, the solution acidified with 17 ml of 4 N anhydrous ethanolic hydrogen chloride and seeded with a few crystals of the resulting salt. The mixture is allowed to stand at room temperature for 5 hours and at −10° overnight. The precipitate formed is filtered off, washed with 25 ml of cold 2-propanol and 8.1 g thereof refluxed in 100 ml of 2-propanol and about 10 ml of water until dissolution takes place. The solution is again slowly cooled to −10°, the precipitate is filtered off and washed with water and diethyl ether, to yield the l-erythro-2R-[2-(4-phenyl-2R-butylamino)-1S-hydroxyethyl]-1,4-benzodioxan hydrochloride melting at 200°–202°, $[\alpha]_D^{25} = -13.5°$ (in dimethylsulfoxide).

The starting material is prepared as follows:

To 2 lt of refluxing water, 3 ml of 40% aqueous tetrabutylammonium hydroxide, 250 ml of salicylaldehyde and 280 ml of trans-1,4-dichloro-2-butene are added while vigorously stirring, followed by the dropwise addition of the solution of 83 g of sodium hydroxide in 400 ml of water at such a rate that the pH of the mixture is kept between 7 and 8 (for 25 minutes). Thereafter the mixture is refluxed for about 6 minutes until the pH is about 7, cooled to 20° and the aqueous layer is extracted with diethyl ether. The extract is combined with the organic layer, washed with 5% aqueous sodium hydroxide, dried, evaporated, the residue distilled and the fraction boiling at 141°–147°/0.7 mmHg collected to yield the 2-(4-chloro-trans-2-butenyloxy)-benzaldehyde.

To the solution of 155.7 g thereof in 3.8 lt of methylene chloride 357 g of 85% 3-chloroperbenzoic acid are added and the mixture is stirred for one hour and refluxed for 4 days. It is cooled, filtered and the filtrate washed with methylene chloride and saturated aqueous sodium bicarbonate, dried and evaporated below 40°, to yield the 2-(4-chlorotrans-2,3-epoxybutyloxy)-phenol formate, showing NMR-peaks at 3.2, 2.5, 4.1, 7.0 and 8.2 ppm.

To the solution of 229.4 g thereof in 900 ml of methanol is added dropwise 1.1 lt of 10% aqueous potassium hydroxide while stirring under nitrogen and maintaining the temperature between 8° and 15°. After stirring at said temperature overnight and at room temperature, the mixture is decanted from the residue and extracted with diethyl ether. The combined residue and extract is washed with water, dried, evaporated and the residue recrystallized from diethyl ether to yield the d,l-erythro-2-oxiranyl-1,4-benxodioxan, melting at 50°–53°.

To the solution of 300 g of l-mandelic acid ($[\alpha]_D^{25} = -147.3°$ in water) in 3.5 lt of anhydrous ethanol 118.4 g of glacial acetic acid are added while stirring, followed by 630.6 g of 93.4% pure d,l-3-amino-1-phenylbutane, the vessel of which is washed with 400 ml of said ethanol. The mixture is stirred for 6 hours at room temperature and 20 hours at 5°, whereupon it is filtered. The residue is washed with 200 ml of petroleum ether and dissolved in 1.1 lt of hot ethanol. It is allowed to cool to room temperature for 19 hours, filtered and the residue washed with 100 ml of said ethanol, to yield the d-3-amino-1-phenyl-butane l-mandelate melting at 140°–142°.

228 g thereof are dissolved in the minimum amount of water, the solution is basified with 15% aqueous sodium hydroxide and extracted with methylene chloride. The extract is washed with water, dried and evaporated, to yield the l-3R-amino-1-phenyl-butane, $[\alpha]_D^{25} = -7.0°$ (ethanol). The hydrochloride thereof shows an $[\alpha]_D^{25} = +7.23°$ (in water), i.e., salt formation reverses the sign of rotation.

The absolute configuration of said 2R-[2-(4-phenyl-2R-butylamino)-1S-hydroxyethyl]-1,4-benzodioxan hydrochloride can be determined as follows: The mother liquors thereof, containing its expected S, R, R-diastereomer [the 4-phenyl-2R-butylamino portion thereof has been elucidated in Rec. Trav. Chim. 82, 189 (1963) already], is evaporated and 1 g of the residue is dissolved in 20 ml of ethanol and 10 ml of water. The solution is combined with that of 0.85 g of sodium metaperiodate in 10 ml of water and the mixture allowed to stand for 24 hours at room temperature. It is filtered, the filtrate evaporated and the residue taken up in 20 ml of ethanol. The solution is combined with 0.2 g of sodium borohydride and the mixture stirred at room temperature for one hour. It is evaporated, the residue taken up in 100 ml of diethyl ether and 20 ml of ethyl acetate and the solution washed with N-hydrochloric acid. The organic layer is dried, evaporated and the residue subjected to gas-chromatography at 160°, to yield the 2R-hydroxymethyl-1,4-benzodioxan with $[\alpha]_D^{25} = +33.4°$ (ethanol), the absolute configuration of which is described in J. Med. Chem. 20, 880 (1977). Considering the sequence rules [Experientia 12, 81 (1956)], said mother liquor contains the d-erythro-2S-[2-(4-phenyl-2R-butylamino)-1R-hydroxyethyl]-1,4-benzoxodioxan hydrochloride, the diastereomer of which, corresponding to Formula I, must be the R,S,R-stereoisomer.

EXAMPLE 2

The mixture of 3.75 g of d,l-erythro-2-oxiranyl-1,4-benzodioxan amd 3.5 g pf 2R-amino-1-p-methoxyphenylpropane [J. Med. Chem. 16, 480 (1973)] is heated to 100° for 4 hours while stirring. It is poured into 25 ml of isopropanol, the solution acidified with 4 N ethanolic hydrogen chloride and the precipitate collected. It is recrystallized from isopropanol, to yield the l-erythro-2R-[2-(3-p-methoxyphenyl-2R-propylamino)-1S-hydroxyethyl]-1,4-benzodioxan hydrochloride melting at 161°–163°; $[\alpha]_D^{25} = -39.2°$ (dimethylsulfoxide).

EXAMPLE 3

According to the method described in the previous examples, the following compounds of Formula I are obtained from equivalent amounts of the corresponding starting materials: X=H, m=q=1.

| No. | n | Y | Salt |
| --- | --- | --- | --- |
| 1 | 1 | H | hydrochloride |
| 2 | 1 | p-OH | hemifumarate |
| 3 | 1 | o-OCH$_3$ | methanesulfonate |
| 4 | 2 | p-OCH$_3$ | hydrochloride |
| 5 | 2 | p-F | " |

EXAMPLE 4

The mixture of 3 g of d,l-erythro-2-oxiranyl-1,4-benzodioxan and 2.8 g of R-3-(m-methoxyphenyl)-2-propylamine is stirred at 100° for 3 hours. After cooling, it is dissolved in 10 ml of isopropanol and the solution acidified with 4 N ethanolic hydrogen chloride. Addition of diethyl ether causes crystallization to yield the 1:1 mixture of R—S—R— and S—R—R— 2-[2-(3-m-methoxyphenyl-2-propylamino)-1-hydroxyethyl]-1,4-benzodioxan hydrochloride melting at 110°–115°.

The starting material is prepared in the following manner: The mixture of 33.5 g of m-methoxyphenylacetone, 25 g of d-α-methylbenzylamine and 120 ml of benzene is refluxed for 24 hours with azeotropic removal of the water formed (3.5 ml). It is evaporated, the residue dissolved in 20 ml of ethanol and the solution hydrogenated over 20 g of Raney nickel at 50° and 3.1 atm. until one molar equivalent of hydrogen has been absorbed. The mixture is filtered, the filtrate evaporated, the residue taken up in 100 ml of isopropanol and the solution acidified with ethanolic hydrogen chloride. The precipitate formed is recrystallized three times from ethanolisopropanol to a constant rotation and melting point to yield the N-d-α-methylbenzyl-m-methoxyphenyl-2-propylamine hydrochloride, $[\alpha]_D^{25} = +19.16°$ (2% in methanol), m.p. 230° (dec.).

The solution of 16 g thereof in 120 ml of ethanol and 30 ml of water is hydrogenated over 5 g of 10% palladium on carbon and 3.1 atm. until one molar equivalent of hydrogen has been absorbed. The mixture is filtered, evaporated, the residue taken up in water and the solution made basic with sodium hydroxide. It is extracted with methylene chloride, the extract dried and evaporated to yield the R-3-(m-methoxyphenyl)-2-propylamine as an oil.

EXAMPLE 5

The mixture of l-erythro-2R-[2-(3-p-methoxyphenyl-2R-propylamino)-1S-hydroxyethyl]-1,4-benzodioxan hydrochloride and 10 ml of 48% aqueous hydrobromic acid is refluxed for thirty minutes and evaporated. The residue is dissolved in 10 ml of water, the solution adjusted to pH=8 with ammonium hydroxide and extracted with ethyl acetate. The extract is dried, evaporated, the residue taken up in 10 ml of hot isopropanol and neutralized with fumaric acid. The precipitate formed after cooling to room temperature is filtered off to yield the l-erythro-2R-[2-(3-p-hydroxyphenyl-2R-propylamino-1S-hydroxyethyl]-1,4-benzodioxan fumarate melting at 200°–205°, $[\alpha]_D^{25} = -40.61°$ (2% in dimethylsulfoxide).

EXAMPLE 6

The mixture of 2.45 g of d,l-erythro-2-oxiranyl-1,4-benzodioxan and 2.3 g of R-3-(p-fluorophenyl)-2-propylamine is stirred at 100° for 3 hours. On cooling it is dissolved in 20 ml of hot isopropanol and the solution acidified with 4 N ethanolic hydrogen chloride. The mixture is slowly cooled, filtered and the residue recrystallized from aqueous isopropanol to yield the l-erythro-2R-[2-(3-p-fluorophenyl-2R-propylamino-1S-hydroxyethyl]-1,4-benzodioxan hydrochloride melting at 238°–240° (dec.); $[\alpha]_D^{25} = -11.97°$ (2% in DMSO).

The starting material is prepared as follows: To the solution of 10 g of racemic R-S-3-(p-fluorophenyl)-2-propylamine in 50 ml of hot isopropanol is added 12 g of l-2-benzodioxanylacetic acid. The precipitate formed on cooling, is filtered off and recrystallized from isopropanol. It is dissolved in the minimum amount of water, the solution made basic with sodium hydroxide, extracted with methylene chloride, the extract dried and evaporated, to yield the R-3-(p-fluorophenyl)-2-propylamine; the hydrochloride thereof melts at 142°, $[\alpha]_D^{25} = +6.25°$ (2% in water).

EXAMPLE 7

Preparation of 10,000 tablets each containing 10.0 mg of the active ingredient:

| Formula: | |
|---|---|
| 2R-[2-(4-phenyl-2R-butylamino)-1S-hydroxyethyl] 1,4-benzodioxan hydrochloride | 100.00 g |
| Lactose | 1,706.00 g |
| Corn starch | 90.00 g |
| Polyethylene glycol 6,000 | 90.00 g |
| Talcum powder | 90.00 g |
| Magnesium stearate | 24.00 g |
| Purified water | q.s |

Procedure:

All the powders are passed through a screen with openings of 0.6 mm. Then the drug substance, lactose, talcum, magnesium stearate and half of the starch are mixed in a suitable mixer. The other half of the starch is suspended in 45 ml of water and the suspension added to the boiling solution of the polyethylene glycol in 180 ml of water. The paste formed is added to the powders, which are granulated, if necessary, with an additional amount of water. The granulate is dried overnight at 35°, broken on a screen with 1.2 mm openings and compressed into tablets using concave punches with 7.1 mm diameter, uppers bisected.

EXAMPLE 8

Preparation of 10,000 capsules each containing 25 mg of the active ingredient:

| Formula: | |
|---|---|
| 2R-[2-(3-p-methoxyphenyl-2R-propylamino)-1S-hydroxyethyl]-1,4-benzodioxan hydrochloride | 250.0 g |
| Lactose | 2,350.0 g |
| Talcum powder | 150.0 g |

Procedure:

All the powders are passed through a screen with an opening of 0.6 mm. Then the drug substance is placed in a suitable mixer and mixed first with the talcum, then with the lactose until homogeneous. No. 2 capsules are filled with 300 mg of the mixture, using a capsule filling machine.

What is claimed is:

1. Specific stereoisomers of erythro-2-(2-aralkylamino-1-hydroxyethyl)-1,4-benzodioxans corresponding to Formula I

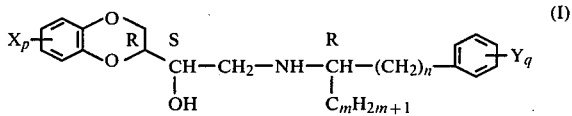

wherein each of X and Y are hydrogen, hydroxy, lower alkyl, lower alkoxy, lower alkylthio, halogen or trifluoromethyl; each of p and q is the integer 1 or 2 and each of m and n is an integer from 1 to 4; or pharmaceutically acceptable acid addition salts thereof.

2. A compound as claimed in claim 1, in which formula each of X and Y are hydrogen, hydroxy, fluoro, chloro, trifluoromethyl or alkyl, alkoxy or alkylthio each with up to 4 carbon atoms, p is the integer 1, p is 1 or 2, and each of m and n is the integer 1 or 2; or pharmaceutically acceptable acid addition salts thereof.

3. A compound as claimed in claim 1, and corresponding to Formula II

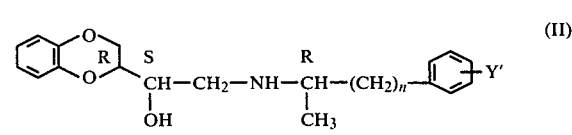

wherein Y' is hydrogen, hydroxy, alkyl or alkoxy with up to 4 carbon atoms and n is the integer 1 or 2; or pharmaceutically acceptable acid addition salts thereof.

4. A compound as claimed in claim 3 and being the l-erythro-2R-[2-(4-phenyl-2R-butylamino)-1S-hydroxyethyl]-1,4-benzodioxan, or pharmaceutically acceptable acid addition salts thereof.

5. A compound as claimed in claim 3 and being the l-erythro-2R-[2-(3-p-methoxyphenyl-2R-propylamino)-1S-hydroxyethyl]-1,4-benzodioxan, or pharmaceutically acceptable acid addition salts thereof.

6. An antihypertensive pharmaceutical composition comprising a hypotensively effective amount of a compound as claimed in claim 1, together with a pharmaceutical excipient.

7. A method of treating hypertension and cardiac conditions in mammals, which comprises administering to them enterally or parenterally a composition as claimed in claim 6.

* * * * *